United States Patent
Orszulak et al.

Patent Number: 6,068,627
Date of Patent: *May 30, 2000

[54] SMART RECOGNITION APPARATUS AND METHOD

[75] Inventors: James Henry Orszulak, Nederland; Gary Lee Dobbins, Jr., Longmont, both of Colo.

[73] Assignee: Valleylab, Inc., Boulder, Colo.

[*] Notice: This patent issued on a continued prosecution application filed under 37 CFR 1.53(d), and is subject to the twenty year patent term provisions of 35 U.S.C. 154(a)(2).

[21] Appl. No.: 08/988,362

[22] Filed: Dec. 10, 1997

[51] Int. Cl.$^7$ ............................................ A61B 17/39
[52] U.S. Cl. .................................... 606/34; 607/1
[58] Field of Search .................. 606/34, 37, 1, 606/4, 10–12; 607/1

[56] References Cited

U.S. PATENT DOCUMENTS

| | | | |
|---|---|---|---|
| 5,157,603 | 10/1992 | Scheller et al. | 364/413.01 |
| 5,342,356 | 8/1994 | Ellman et al. | 606/32 |
| 5,396,062 | 3/1995 | Eisentraut . | |
| 5,400,267 | 3/1995 | Denen . | |
| 5,413,573 | 5/1995 | Koivukangas . | |
| 5,434,398 | 7/1995 | Goldberg . | |
| 5,605,150 | 2/1997 | Radons et al. | 128/360 |
| 5,625,370 | 4/1997 | D'Hont . | |
| 5,651,780 | 7/1997 | Jackson . | |
| 5,660,567 | 8/1997 | Nierlich . | |

FOREIGN PATENT DOCUMENTS

WO 96/08794  3/1996  WIPO .

*Primary Examiner*—Linda C. M. Dvorak
*Assistant Examiner*—Roy Gibson

[57] ABSTRACT

A qualifying connection for an instrument attaches to a source of electrosurgery energy to and the instrument and has first and second parts coupled to the instrument and the source, respectively. Optical couplings on the connection transmit invisible energy to identify the instrument and are proximate on the first and second parts. A light modifier on the first part is proximal to the second part for modification of radiation in the infrared wavelengths so infrared transmitters encode signals and non contact coded proximity detectors on the second part are the coupled detectors. Non contact coded proximity detectors respond to modified infrared light establishing an Nth bit identification code. An infrared light supply in the source pass from the transmitters across the communicating couplings for encoding signals by modification of the infrared light with a light modifier. Mechanical attachments include conjugating male and female portions physically extending between the parts for mating engagement. The attachments juxtaposition the parts when the attachments geometrically conjugate to geographically positioning the couplings proximate for communicating. The attachments have one or more conductors for delivery of high frequency energy from the source to the instrument. A cable fits between the first part of the connection and the instrument and has electrical conductors for carrying energy passing through the first part of the connection from the source to the instrument. An identifying circuit couples to the second part and responds to invisible light optically communicated across the couplings for verifying the type of instrument connected by the cable to the source.

48 Claims, 2 Drawing Sheets

SMART RECOGNITION APPARATUS AND METHOD

FIELD OF THE INVENTION

This relates to a smart recognition system for electrosurgery and a qualifying connection with non contact, coded proximity detection, using diffuse surface, infrared reflective coupling as an instrument identification process. More particularly, the system identifies, qualifies or verifies the correct connection between a source of high frequency energy and an instrument.

BACKGROUND OF THE DISCLOSURE

Electrosurgery requires controlled application, with an instrument, of radio frequency energy to an operative tissue site. To achieve successful clinical results during surgery, the electrosurgical generator, as the source of the high frequency or radio frequency energy, should be mated correctly with an appropriate instrument for a specific surgery. Due to the variety of operative electrosurgical procedures requiring various levels of radio frequency energy delivery from an attached instrument, problems arise with mismatching an electrosurgical generator and the instrument. The operating rooms with a variety of instruments and generators available for surgery create a potential for mismatch problems and thus may increase the patient risk.

U.S. Pat. No. 5,400,267 discloses a system with a non volatile memory with an EEPROM in the instrument or its attached cable. The memory identifies the instrument. A problem arises when the memory is located external to the power supply requiring hardwire connections. The communicated data transmission from the memory to the control may have an error due to radiated emissions from radio frequency energy wires located closely when delivered by the electrosurgical generator during surgery. Radio frequency exposure will interfere with the identification information being transmitted so it becomes difficult to determine that the correct medical instrument is attached to the power source. In addition a further problem is presented because the memory means must be located in the reusable part of the medical instrument. For purposes of instrument identification, this patent restricts application to reusable medical instruments and prohibits an instrument identification for low cost disposables.

U.S. Pat. No. 5,413,573 describes identification of surgical instruments by incorporating a unique interface between two components such that their engagement by two surfaces defines the identity of an instrument if properly mated. In this system, a switch is provided on a component first surface called the orientation means. A second surface incorporates a contact on an intermediate component. Upon engagement of these two components the appropriate switch and contact mating establish the given identity. A problem arises with this approach, as the integrity of the identity depends on the engagement with the mating of components. A degradation of this identification occurs, with repeated engagements causing deterioration of the mating switch to contact interface between components. A secondary problem also occurs from the multiple engagement process as this approach requires a specific orientation alignment between mating surfaces. As the numbers of switch to contact interfaces increase, a tighter tolerance must be maintained between mating surfaces to retrieve the identity information. Repeated component engagements will also deteriorate this orientation alignment and thus degrade the accuracy in maintaining the identity.

U.S. Pat. No. 5,434,398 uses a magnetic encoding process to establish the identity with a card based system. Modulated magnetic fields embedded in a smart card require the use of a ferromagnetic element to retain the unique identity code. A magnetic reader decodes the card information allowing system activation. Exposure of this system to radio frequency energy used in electrosurgery, could effect the integrity of the magnetic smart card and degrade the ability of the magnetic based card reader to accurately decode its proper identity. Radio frequency energy would remagnetize both the smart card and reader by induced magnetic coupling to the ferromagnetic elements. Clearly this system would require magnetic shielding to retain identity data. Indeterminate magnetic sources present in the operating room also creates additional major problems for this system and would make its use in electrosurgery suspect.

U.S. Pat. No. 5,396,062 describes a power source receptacle system with detection of the presence of a mated plug, by using an optical coupling technique, established by beam passage through the receptacle. This approach uses a light emitter to generate a beam, that passes through openings in the receptacle contacts, to a receiver aligned on a dedicated optical axis. A powered instrument having a bladed plug for insertion in a receptacle breaks the beam transmission path sending a corresponding signal to a controller that detects the plug engagement. The '062 patent is limited in use, in that, it provides for detection when a mating plug is either inserted or removed from the receptacle. Power can only be activated or deactivated in the receptacle, based on whether the mating plug is engaged or disengaged. Numerous problems are presented by this system. First, the identity is not recognized or associated to a given instrument plugged into the receptacle. Second, the power applied to the receptacle cannot be differentiated between specific pluggable instruments. Also, additional problems are presented, because a specific optical axial alignment is required for beam passage, through the openings in the power receptacle contacts, thereby requiring a specific mechanical alignment integrity. U.S. Pat. No. 5,625,370 has an electromagnetic device and method in an identification system apparatus. An electrically conductive material is disposed to pass through a magnetic flux loop of the electromagnetic device. The coupling established between those components is the means by which identification information is transferred. An antenna may also be electrically connected to the conductive material to augment the apparatus for receiving transmitted identification information. Multiple identification problems exist with radio frequency based equipment due to radiation coupling with the electromagnetic conductive strip and antenna which will deteriorate the identity signals. Error borne signals lose their identity and become inaccurate with decoding. The radio frequency energy may also electromagnetically couple to distort the magnetic flux loop of the electromagnetic device. This will reduce the signal to noise ratio during information transfer and lower the accuracy of the identity information recovered.

International Patent WO9608794 has a security code identification circuit that uses a radio frequency based card reader and decoder method to recover a digital security code. The card reader includes a receiving antenna sensitive to a signal generated to an access card. A receiver circuit is coupled to the receiving antenna to detect and process an analog signal that is then converted to a digital security code. A problem with this type of recognition system makes it error borne and unacceptable for code identification in radio frequency systems. Radio frequency energy contains components that will be picked up and coupled by the reader receiving antenna as it is sensitive to those frequencies. This will confuse the card reader antenna and detector electronics. Erroneous signal components will be processed along with the identification signal; thus, generating errors in the detected signal. The recognition system digital security code could not be a true representation of the signal information and thus identification is inaccurate for use with radio frequency based equipment.

U.S. Pat. No. 5,660,567 has a smart connector for a sensor with removable encoding medical device. The smart identification method is accomplished within the connector module pin interconnect wherein a dedicated group of removable pins from a multiple pin connector are used to attach an encoding device read by the sourcing equipment. The sensor, attached to this connector with encoding device, identifies the medical device. The smart connector distinguishes either a resistor, an electronic device, a memory device or a modulating device to identify the medical device. Insertion and removal of an encoder requires assembly, thereby making the accuracy and repeatability of the identification process suspect and prone to error. Recovery of the smart signal interface is dependent on the reliability of the electrical and mechanical connections required as mechanical misregistration and intermittent electrical contacts will degrade accuracy. In applications where radio frequency energy exists proximate to the encoding, the corruption of electronic signals used for identity recognition will result. Radio frequency energy will radiate and conductively couple with electronic or memory devices to reduce the accuracy of decoded signals.

U.S. Pat. No. 5,651,780 has an identification and monitoring method for recognizing the physical and or functional characteristics of medical devices. Identification means located within the medical instrument uses an electronic memory such as a non-volatile AM ROM, EEPROM or EPROM. Information is stored about the medical device attributes look-up tables within a power source include an acceptable device list or performance characteristic to compare to the attached instrument to determine application use. The identification teachings of this patent are similar to the one identified in U.S. Pat. No. 5,400,267. The problems with '780 are similar to those mentioned for the '267 patent.

A solution to the above problems is disclosed and claimed herein and it addresses the noted limitations of the patents discussed. A smart recognition system for electrosurgery includes a smart connector sensing topology. In addition to uniquely recognizing the correct mating of electrosurgical power sources with the attached pluggable medical instruments the smart connector sensing approach herein provides a solution that has inherent immunity to the problems discussed. The present system has the smart identification code integral to the connector assembly to avoid assembly errors. Use of a non-contact, optical method smart signal recovery eliminates electrical contact degradation and mechanical misalignment problems. An infrared diffuse reflectance code identification recovery method which has inherent accuracy and reliability in harsh, high power radio frequency electrosurgical environments and application in fields outside electrosurgery.

SUMMARY OF THE INVENTION

The preferred embodiment of the smart connector sensing approach has a non-contact, coded proximity detector that uses a diffuse surface, infrared reflective coupling. Delineation of this smart sense topology yields benefits providing the immunity referenced as an intrinsic property of the means used. A non contact technique avoids problems associated with mechanical alignment, component engagement and part mating orientation. Physical contact for sensing between mating components is not required for identity recognition. Coded proximity detection provides a unique identity association between plugged medical instruments and Rf energy sources. Multiple integrated optical paths, each containing both emitting and receiving components, proximally detect a unique Nth bit code identification for each medical instrument, plugged into an Rf energy source. Identification problems, associated with memory communication and data storage and registration and fatigue problems caused by component engagement alignment problems of multiple sensors for code identity, are avoided.

A light coupled, non-magnetic approach, avoids instrument identity problems with electromagnetic (EMI) interference. Light coupled identity sensing is immune to this noise. A light coupled technique, also avoids problems caused by electrical discontinuity, due to a mechanical disconnection of wire contacts between hardwire connections, or switches. A diffuse surface reflective coupling, avoids problems associated with optical axial alignment and focused optics. Unfocused optical components are preferred to proximally detect plugged instruments with diffuse surface reflection. Optimal smart sense recognition is obtained from non-planer, diffuse surface, including medical instrument plugs located within a proximal range from the smart sense components. As a result, tight optical and mechanical registration tolerances, along with high polished optical surfaces are not required to maximize instrument recognition and signal recovery.

Infrared reflective coupling is preferred as it provides high accuracy sensing and signal recovery for smart recognition, medical instrument detection. Unlike the visible light sensors, that encompass a broad spectrum of light wavelengths, infrared light exists at a narrow band width wavelength. This provides a high accuracy, sensory signal recognition apparatus and method. Infrared offers a high discriminating signal to noise ratio between the smart sense light source and the ambient background light of the operating room. A smart connector sensing approach has maximum flexibility for medical instruments. Disposable and reusable medical instruments, may be uniquely identified and attached to an electrosurgical Rf generator source, for clinical use. A smart recognition system for electrosurgery is herein presented. The benefits described are unique medical applications for electrosurgery. In addition, the approaches for applications outside electrosurgery are possible as example: lasers, microwaves, ultrasonics and fluid based energy delivered systems.

The smart recognition system for electrosurgery provides an accurate medical instrument identification, for instruments attached to an electrosurgical generator source of high frequency electrosurgical energy. A control of the application of Rf energy during surgical procedures is also disclosed. Specific Rf power levels developed in the electrosurgical generator may be uniquely activated and coupled to individually recognized medical instruments for performing electrosurgery. Activation and surgical use of the Rf energy source are only allowed with an appropriate validation from the smart recognition system.

This occurs when the proper medical instrument has been attached to the electrosurgical generator. Using this approach to control the power source for a particular tissue and to achieve the desired clinical effect prevents misapplication of Rf energy to the patient. As a result, the risk of patient injury is minimized and safety increased.

DETAILED DESCRIPTION OF IRE INVENTION

Figure 1:
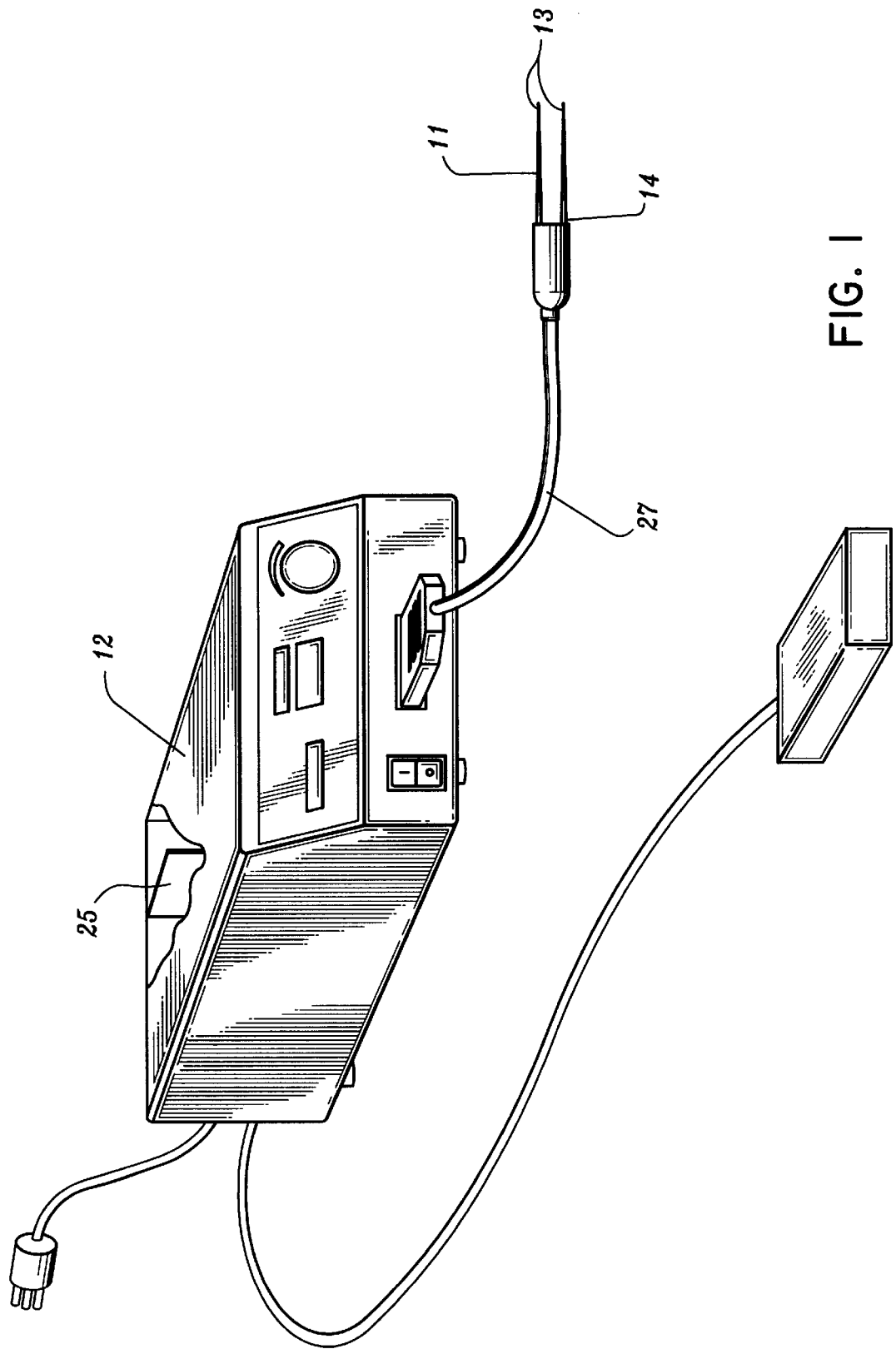
FIG. 1 is a perspective view of the smart recognition system with a source of medical treatment, a qualifying connection and attached instrument.

A qualifying connection 10 is disposed between an instrument 11 and a source of medical 12 treatment for passage of treatment energy from the source of medical treatment 12 through the qualifying connection 10 to the instrument 11 and to a patient. The qualifying connection 10 selectively permits passage of information from the instrument 11 to the source of medical treatment 12 in FIGS. 1 and 2. The qualifying connection 10 includes the instrument 11 having a distal end 13 for treatment of the patient and a proximal end 14 for manipulation by a surgeon. The instrument 11 is connected to the qualifying connection 10. The source of medical treatment 12 provides energy delivery to the instrument 11. The source of medical treatment 12 is attached to the qualifying connection 10. A first part 15 of the qualifying connection 10 connects to the instrument 11 in FIG. 2. A second part 16 of the qualifying connection 10 is carried on and connected to the source of medical treatment 12. Optical couplings 17 and 18 on the qualifying connection 10 extend between the first and second parts 15 and 16 respectively to pass optical energy thus communicating information in the form of the identity of the instrument 11 to the source of medical treatment 12.

Figure 2:
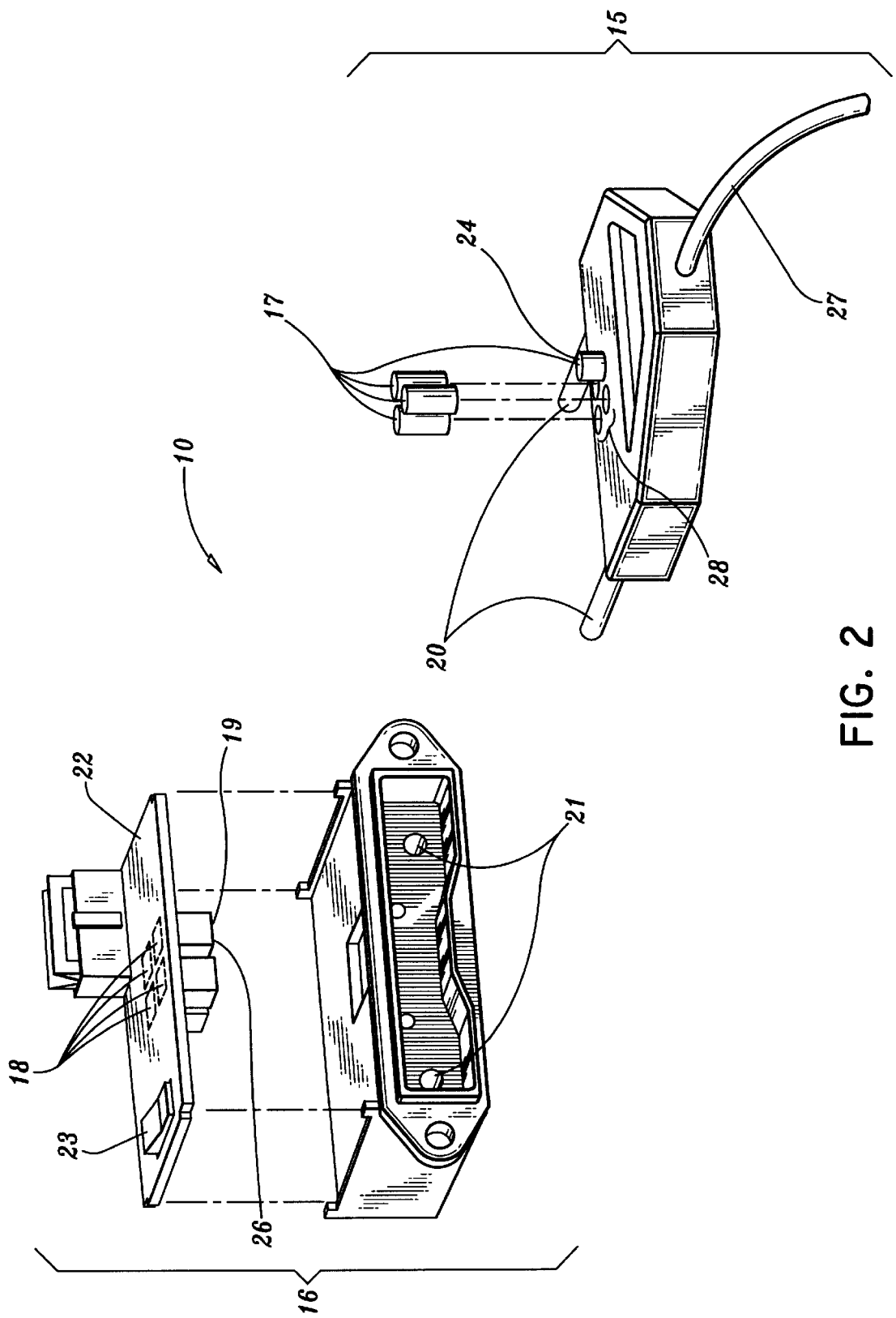
FIG. 2 is a side view of the connector of FIG. 1 enlarged and in cross section for showing the relative relationships of the optical couplings and the mechanical attachments of first and second parts of the qualifying connection.

A light supply 19 is in the source of medical treatment 12 is part of the qualifying connection 10 for transmitting across the communicating optical couplings 17 and 18 shown in FIG. 2. The light supply 19 operates within a predetermined wavelength. Mechanical attachments 20 and 21 across the qualifying connection 10 juxtaposition the first and second parts 15 and 16 thereof. The mechanical attachments 20 and 21 have geometric mechanical conjugations for delivering medical treatment through the qualifying connection 10 from the source of medical treatment 12 to the instrument 11. The mechanical attachments 20 and 21 position geographically the optical couplings 17 and 18 in proximity to communicate between the first part 15 on the instrument 11 and the second part 16 on the source of medical treatment 12 when the mechanical attachments 20 and 21 conjugate so the optical couplings 17 and 18 may communicate the information as an indication of the identity of the instrument 11 connected to the source of medical treatment 12.

An identifying circuit 22, a circuit board in the source of medical treatment 12 and on the second part 16 responds to the information as the indication of light optically communicated through the optical couplings 17 and 18 thereby differentiating the type of instrument 11 connected by the mechanical attachments 20 and 21 through the qualifying connection 10 to the source of medical treatment 12. The identifying circuit 22 in FIG. 2 signals verification to the source of medical treatment 12. A switch 23, preferably a comparator integrated circuit, is connected to the identifying circuit 22 in the source of medical treatment 12. The switch 23 responds to the signaling of the identifying circuit 22. The switch further connects within the source of medical treatment 12 for enabling the passage of medical treatment 12 from the source of medical treatment 12 through at least one of the mechanical attachments 20 or 21 and to the instrument 11.

Conjugating male and female portions may be one form of the mechanical attachment 20 and 21 as shown in FIG. 2. The male and female portions physically extend between the first and second parts 15 and 16 across the qualifying connection 10 for mating engagement. The optical couplings 17 and 18 positioned on the first and second parts 15 and 16 are preferably aligned in proximate relation for communication therebetween upon the mating engagement of the mechanical attachments. The optical coupling 17 on the first part 15 includes a light modifier 24. The light modifier 24 includes either a diffuse surface in the form of a coating, a matrix of holes or another preselected light responsive material to modify the wavelength of radiation affected by the light modifier 24 for thereafter receipt by the optical coupling 18 on the second part 16 for signaling the source of medical treatment 12, see FIG. 2.

The mechanical attachments 20 and 21 include one or more male portions on the first part 15 for conjugation. The mechanical attachments 20 and 21 include one or more female portions on the second part 16 for conjugation. Of course the male and female portions could be reversed or alternated. The first part 15 of the optical couplings 17 and 18 includes the light modifier 24 indicative of the type of instrument 11 connected to the first part 15. Infrared transmitters as a preferred light supply 19 are positioned on the second part 16 proximal the light modifier 24 for optical communication of the light therethrough. The source of medical treatment 12 is preferably a source of high frequency energy, but could be a laser, hydro disector, aspiration or other medical or surgical delivery system. A memory 25 with the source of medical treatment receives the information as the indication in the form of modified light energy from the optical couplings 17 and 18 best shown in FIG. 1. The memory 25 compares the light transmitted through the optical couplings 17 and 18 modified thereby with information. The memory 25 receives the information and controls the activation or deactivation of the energy source 12. The optical couplings 17 and 18 preferably include a diffuse surface infrared reflector as the preferred light modifier 24 on the first part 15 and non contact coded proximity detectors 26 as part of the light supply 19 on the second part 16 responsive to the light returned from the diffuse surface infrared reflector 24 communicated as information indicative of the instrument 11 identification for the identifying circuit 22.

A method of using the qualifying connection 10 for the instrument 11 attached to source of high frequency energy 12 for electrosurgery and for delivering surgical signals from the source of high frequency energy 12 through the qualifying connection 10 to and from the instrument 11 has first and second parts 15 and 16. The method has steps including juxtapositioning the first and second parts 15 and 16 across the qualifying connection 10 with mechanical attachments 20 and 21 and optical couplings 17 and 18 therebetween. Conjugating the first and second parts 15 and 16 on the qualifying connection 10 with geometric mechanical attachments 20 and 21 and transmitting invisible optical energy across optical couplings 17 and 18 juxtaposed by first and second parts 15 and 16 of the qualifying connection 10 for communicating instrument 11 identity with invisible light supplied from the source of high frequency energy 12 are steps of the method. The method has the step of modifying the invisible optical energy with geographically disposed proximate optical couplings 17 and 18 of the first and second parts 15 and 16 when the mechanical attachments 20 and 21 engage so the optical couplings 17 and 18 are proximate. Communicating the type of instrument 11 connected by a cable 27 between the first part and the instrument 11, by passing a signal of the modified invisible optical energy through the qualifying connection 10 and to identifying circuit 22 in the source of high frequency 12 is a method step. A step of the method is assessing the modified invisible optical energy from the optical couplings 17 and 18 with the identifying circuit 22 for use as verification for controlling the source of high frequency energy 12. A method step is enabling the flow of high frequency energy 12 from the source of high frequency energy 12 through at least one of the mechanical attachments 20 or 21, the cable 27 and to the instrument 11 with switch 23 in the source of high frequency energy 12 responsive to control from the identifying circuit 22. Carrying high frequency energy through the mechanical attachments 20 and 21 from the source of high frequency energy 12 to the instrument 11 and through cable 27 between the first part 15 of the qualifying connection 10 and the instrument 11 is a step.

The method has a step of conjugating male and female portions that form the mechanical attachments 20 and 21 by physically extending the mechanical attachments 20 and 21 between the first and second parts 15 and 16 across the qualifying connection 10 during mating engagement. The method includes the step of communicating between the optical couplings 17 and 18 by transmitting optical energy as signals from the second part 16 as encoded in modified invisible optical energy by light modifier 24 on the first part 15 sensed by detectors 26 on the second part 16 positioned proximate by the mating engagement of the mechanical attachments 20 and 21. The method has the step of modifying invisible light radiation in the infrared wavelengths by a diffuse surface as the light modifier 24. The method includes the step of modifying the invisible light radiation with a matrix 28 on the first part and infrared emitters on the second part positioned proximate to the matrix 28 for coding signals. The matrix 28 is preferably a combination of diffuse reflectors and holes in coupling 17 of first part 15 as in FIG. 2. The method has the step of receiving the coded signals before activating or deactivating the source of high frequency energy 12 with switch 23 coupled to memory 25 in the identifying circuit 22 wherein the memory 25 compares the coded signals to predetermined instrument 11 identification therein. The method has the step of communicating through optical couplings 17 and 18 by non contact, coded proximity detectors responsive to diffuse surface invisible infrared optical energy for instrument 11 identification.

The qualifying connection 10 for instrument 11 in a preferred embodiment attaches to source of high frequency energy 12 for electrosurgery. Surgical signals from the source of high frequency energy 12 are delivered through qualifying connection 10 to and from instrument 11. First part 15 couples to instrument 11 and second part 16 is in the source of high frequency energy 12. Mechanical attachments 20 and 21 on first and second parts 15 and 16 geometrically conjugate. The mechanical attachments 20 and 21 extend across the qualifying connection 10 for juxtapositioning first and second parts 15 and 16. Mechanical attachments 21 on second part 16 connect to source of high frequency energy 12. Mechanical attachment 20 on first part 15 couples to instrument 11 for delivery of high frequency energy 12 and therefore are electrical conductors. Optical couplings 17 and 18 on first and second parts 15 and 16 pass invisible optical energy thereacross to communicate instrument 11 identity. Optical couplings 17 and 18 geographically orient proximate relative to the juxtaposed first and second parts 15 and 16 for communicating when the mechanical attachments 20 and 21 conjugate. Infrared light supply 19 in source of high frequency energy 12, connects through optical couplings 17 and 18 in the transmission across the communicating optical couplings 17 and 18. Infrared light modifier 24 on optical coupling 17 is positioned proximal for coding of the transmitted infrared light communicated there across.

Cable 27 fitted between first part 15 and instrument 11 carries high frequency energy from mechanical attachments 20 and 21 to instrument 11. Cable 27 allows movement of instrument 11 relative to source of high frequency energy 12. Identifying circuit 22 in source of high frequency energy 12 connects to respond to infrared light optically coded by infrared light modifier 24. Identifying circuit 22 verifies the type of instrument 11 connected by cable 27 through qualifying connection 10 to source of high frequency 12 electrosurgical energy. Identifying circuit 22 connects for signaling the verification to source of high frequency energy 12.

Switch 23 in source of high frequency energy 12 couples to identifying circuit 22 for responding to the signals of identifying circuit 22. Switch 23 connected within source of high frequency energy 12 for enabling and disabling the flow of high frequency energy 12 therefrom and through at least one of mechanical attachments 20 and 21, cable 27 and to the instrument 11.

One form qualifying connection 10 includes first part 15 thereof connected to instrument 11 and second part 16 thereof carried in and connected to source of medical treatment 12. A transmitter such as light supply 19 on source of medical treatment 12 delivers informational energy to first part 15 on instrument 11 and modifier 24 on first part 15 is proximately positioned relative to transmitter 19. Modifier 24 changes the energy from the transmitter 19. One or more receivers such as detectors 26 on second part 16 are located for receipt of the changed energy from modifier 24. Mechanical attachments 20 and 21 across qualifying connection 10 juxtaposition first and second parts 15 and 16 thereof Mechanical attachments 20 and 21 having geometric conjugations deliver medical treatment through qualifying connection 10 from source of medical treatment 12 to instrument 11. Mechanical attachments 20 and 21 position proximally and geographically first part 15 on instrument 11 and second part 16 on source of medical treatment 12 when mechanical attachments 20 and 21 conjugate so that first and second parts 15 and 16 may communicate across qualifying connection 10 between first and second parts 15 and 16 for transmitting and receiving information and modified energy thereacross thus communicating the identity of instrument 11 to and medical treatment from source of medical treatment 12.

Identifying circuit 22 connects to second part 16 located in source of medical treatment 12 for receiving communicated information from receiver 26. Identifying circuit 22 responds to communicated information for differentiating the type of instrument 11 connected by mechanical attachments 20 and 21 through qualifying connection 10 to source of medical treatment 12. Identifying circuit 22 generates a signal of verification to source of medical treatment 12. Switch 23 in source of medical treatment 12 responds to the signaling of identifying circuit 22. Switch 23 connects to identifying circuit 22 within source of medical treatment 12. Switch 23 connects within source of medical treatment 12 for controlling the passage of medical treatment from source of medical treatment 12 through at least one of the mechanical attachments 20 or 21 and to instrument 11.

Switch 23 is connected to an energy provider such as an electrosurgical generator in source of medical treatment 12.

Switch 23 within identifier circuit 22 communicates identification information to allow setting the nature of the energy conveyed in accord with instrument 11 identified and for differentiating instrument 11 attached through qualifying connection 10 from other unqualified instruments 11. Transmitter 19 delivers light in the infrared wavelengths and the modifier 24 is preferrably a surface on first part 15 positioned proximal to transmitter 19 on second part 16. The surface is configured to modify the delivered light by absorption, diffraction, reflection or a combination thereof. Mechanical attachments 20 and 21 preferrable include one or more electrical conductors and the energy provider includes the electrosurgical generator for delivery of modes of radio frequency electrosurgery across the mechanical attachments 20 and 21. Mechanical attachments 20 and 21 include alternatively one or more wave guides when the energy provider is a laser for delivery of light energy through mechanical attachments 20 and 21. Mechanical attachments 20 and 21 include alternatively one or more fluid passages when the energy provider is a fluid movement apparatus for delivery of suction or irrigation through the mechanical attachments 20 and 21. Mechanical attachments 20 and 21 include alternatively one or more energy couplings when the energy provider is a microwave generator for delivery of microwaves through the mechanical attachments 20 and 21. The mechanical attachment 20 and 21 include alternatively male and female portions.

Modifier 24 is located in first part 15 sandwiched between the transmitter 19 and receiver 26 on second part 16. The surface includes matrix 28 for modifying the light in the infrared wavelengths. The receivers 26 may include fiber optics extending between second part 16 and the source of medical treatment 12, detectors located in source of medical treatment 12 connected to the fiber optics so that the space required for the detectors is uninhibited by second part 16. The receivers may include fiber optics extending between second part 16 and source of medical treatment 12. The fiber optics have several groups of multiple redundant fibers for simultaneously passage of the information from modifier 24 in the form of modified light. A plurality of cells such as optical coupling are within source of medical treatment 12 so each group of the multiple redundant fibers may extend to a particular cell and deliver thereto modified light as coded identity information.

The preferred embodiment of the smart recognition system has a smart qualifying connector 10 bipolar jack, smart sense processor, an illuminating display indicator that validates instrument 11 recognition, and a medical instrument. There is a mating plug and surgical instrument 11, attached by a connective cable. The medical instrument plug may establish an Nth bit code identity. The smart connector bipolar jack is preferably located on the front panel of the electrosurgical generator. The bipolar jack is preferably the power receptacle through which the electrosurgical generator outputs the Rf energy to an attached medical instrument. Rf energy output can only occur after the smart recognition identity of the medical instrument has been correctly established. Physical configuration of the connector is preferably asymmetric to allow a unidirectional attachment of the medical instrument. This conditional mating, automatically facilitates the proper orientation of the medical instrument plug, so that the infrared proximity detectors can properly decode the medical instrument identity. The bipolar jack is most preferably manufactured from a machined piece of black polymer. This creates a shrouded, dark adaptive, light environment for the infrared sensory components, to recover the maximum signal. The black polymer absorbs the unwanted infrared light, if any, in the operating room and is opaque to visible light preventing reflection, transmission and pickup by the smart sense components.

A rectangular cutout, present in the bipolar jack, may allow the infrared components, mounted on the smart sense processor a viewing aperture window for inspection of the mated medical instrument plug. The identification and verification of compatibility for electrosurgical use results. The smart sense processor mounted on top of the bipolar jack performs the function of coded proximity detection using diffuse surface infrared reflective coupling to the attached medical instrument plug. An Nth bit signal code unique to the instrument 11 attached is recovered. Upon retrieving the medical instrument identity, the information is hardware and software processed to discriminate if the identity code is correct. Discrimination is made to determine if the attached instrument 11 should be supplied Rf energy from the electrosurgical generator. Considering a valid recognition, Rf energy is delivered to a tissue site for surgical use. The smart sensing performs hardware code processing. The smart processor either locally controls the activation of the Rf energy of the generator or transmits the code information to a microcontroller wherein a comparative decision is made relative to the instrument 11 identity.

A display indicator provides visual illumination of a positive bit code recognition, that the correct medical instrument 11 is attached to the electrosurgical generator. The display is located on the front panel of the electrosurgical generator. Display illumination continues as long as the identity of the attached medical instrument is recognized. Removal of the medical instrument plug deactivates the display indicator and prevents any further keyed activation of Rf energy, from the generator output.

The medical instrument has a mating connection and instrument with a connective cable. The plug is preferably an overmolded assembly with pin contacts that mate with a bipolar jack receptacle on the generator for transferring the Rf energy. A matrix of holes and plugs is established between the molded plug and receptacle. The holes and plugs permit infrared light therethrough or reflected to establish the Nth bit identity code unique to the medical instrument. Exposure of the plug to liquids should not ordinarily alter the identity code of the instrument 11. Fluids entering this matrix of holes will pass by gravity due to the vertical orientation of the preferred embodiment of the holes. Fluids present on the plug surface, in the area occupied by the plug insert, should not alter the retrieval process of the identity code, due to the proximity detection by infrared sensors. The unfocused infrared optical sensor responds to the presence of objects with irregular surfaces. Diffraction of light energy due to surface granularity or discontinuities should not contribute significantly to the loss of signal recovered by the infrared sensor. The proximity of the infrared sensor does not obviate the recovery of code information due to adjacent bit cell sites. A rapid fall off the diffractive light energy prevents the corruption of the unique identity code. The accuracy and integrity of the smart recognition system for electrosurgery are preserved.

The medical instrument plug inserts are used to establish the Nth bit code identity for the instrument 11 and are located in the overmolded plug. These plug inserts are constructed of compatible materials to the plug and are fitted and arranged consistent with the identity code selected. The arrangement permits retrieval by the proximity detection method described.

While a particular preferred embodiment has been illustrated and described, the scope of protection sought in the claims that follow covers any connection that uses non environmental radiation across an optical coupling to verify or identify the instrument 11 connected before energy is permitted to pass through the connection from the high frequency generator to the instrument 11.

In addition to the preferred embodiment, which uses non contact, coded proximity identity detection with diffuse surface reflection optical coupling, the scope of claims delineated herein covers enhancements to optical couplings and coding methods with alternate light modifiers and light conduits. This includes as example alternate light modification technology methods using light modulation or matrix encoding methods to generate unique coding algorithms. The use of fiber optics as a light conduit may enhance code identity detection methods with multiple redundant fibers used in specific cell structure orientations so information transmitted provides a unique light discriminator to the diffuse reflection light in the infrared wavelengths. Alternate configurations which strategically reposition the transmitters, receivers and light modifiers to further enhance the coded proximity detection means are in the claims for optimal optical coupling.

What is claimed is:

1. A system including an instrument, a source of high frequency energy and a qualifying connection between the source of medical treatment for passage of treatment energy from the source of medical treatment through the qualifying connection to the instrument and to a patient, the qualifying connection for selectively permitting passage of information from the instrument to the source of medical treatment, the system comprising:

an instrument having a distal end for treatment of the patient and a proximal end for manipulation by a surgeon, the instrument connected to the qualifying connection;

a source of medical treatment for providing energy delivery to the instrument, the source of medical treatment attached to the qualifying connection;

a first part of the qualifying connection connected to the instrument;

a second part of the qualifying connection carried on and connected to the source of medical treatment;

optical couplings on the qualifying connection and on the first and second parts for passing optical energy communicating the information in the form of the identity of the instrument to the source of medical treatment;

a light supply in the source of medical treatment, the light supply connected to the qualifying connection for transmitting across the communicating optical couplings, the light supply within a predetermined wavelength;

mechanical attachments across the qualifying connection for juxtapositioning the first and second parts thereof, the mechanical attachments having geometric mechanical conjugations for delivering medical treatment through the qualifying connection from the source of medical treatment to the instrument, the mechanical attachments for positioning geographically the optical couplings in proximity to communicate between the first part of the instrument and the second part on the source of medical treatment when the mechanical attachments conjugate so the optical couplings may communicate the information as an indication of the identity of the instrument connected to the source of medical treatment;

an identifying circuit in the source of medical treatment, the identifying circuit connected to the second part and responsive to the information as the indication of light optically communicated through the optical couplings thereby differentiating the type of instrument connected by the mechanical attachments through the qualifying connection to the source of medical treatment, the identifying circuit for signaling verification to the source of medical treatment, and a switch connected to the identifying circuit in the source of medical treatment, the switch responsive to the signaling of the identifying circuit, the switch further connected within the source of medical treatment for enabling the passage of medical treatment from the source of medical treatment through at least one of the mechanical attachments and to the instrument.

2. The qualifying connection of claim 1 wherein conjugating male and female portions form the mechanical attachments, the male and female portions physically extend between the first and second parts across the qualifying connection for mating engagement.

3. The qualifying connection of claim 1 wherein the optical couplings positioned on the first and second parts are aligned in proximate relation for communication therebetween upon the mating engagement of the mechanical attachments, the optical coupling on the first part including a light modifier.

4. The qualifying connection of claim 3 wherein the light modifier includes a diffuse surface, a coating, a matrix of holes or a preselected light responsive material to modify the radiation passing through the light modifier for thereafter receipt by the optical coupling on the second part for signaling the source of medical treatment.

5. The qualifying connection of claim 2 wherein the mechanical attachments include one or more male portions on the first part for conjugation.

6. The qualifying connection of claim 2 wherein the mechanical attachments include one or more female portions on the second part for conjugation.

7. The qualifying connection of claim 4 wherein the first part optical couplings include the light modifier indicative of the type of instrument connected to the first part.

8. The qualifying connection of claim 7 wherein infrared transmitters are positioned on the second part proximal the light modifier for optical communication of the light therethrough.

9. The qualifying connection of claim 8 wherein the source of medical treatment is a source of high frequency energy, the identifying circuit including a memory to receive the information as the indication in the form of modified light energy from the optical couplings, the memory for comparing the light transmitted through the optical couplings and modified thereby with information, the memory for receiving the information and controlling the activation or deactivation the source of high frequency energy.

10. The qualifying connection of claim 1 wherein the optical couplings include a diffuse surface infrared reflector on the first part and non contact coded proximity detectors on the second part responsive to the light returned from the diffuse surface infrared reflector communicated as information indicative of the instrument identification for the identifying circuit.

11. A system including a source of high frequency energy and qualifying connection for an instrument attached to the source of high frequency energy for electrosurgery and surgical signals from the source of high frequency energy delivered through the qualifying connection to and from the instrument, the qualifying connection having a first part connectable to the instrument and a second part connected to the source of high frequency energy, the qualifying connection comprising;

optical couplings on the qualifying connection for transmitting invisible optical energy thereacross for communicating instrument identity to the source of high frequency energy, the optical couplings positioned on the first and second parts in proximate relation for communication thereacross;

a light modifier on the first part of the optical coupling, the light modifier positioned proximally to the second part for modification of radiation in the infrared wavelengths;

transmitters of infrared wavelengths encoded signals and non contact coded proximity detectors as the optical couplings positioned on the second part, the non contact coded proximity detectors responsive to infrared modification from the light modifier for providing information indicative of instrument identification;

an invisible light supply in the source of high frequency energy for delivery from the transmitters and across the communicating optical couplings of the infrared wavelength encoded signal for modification by the light modifier to communicate coded signals thereacross;

mechanical attachments including conjugating male and female portions physically extending between the first and second parts across the qualifying connection for mating engagement, the mechanical attachments across the qualifying connection for juxtapositioning the first and second parts, the mechanical attachments geometrically conjugating thereby geographically positioning the optical couplings proximate for communicating, the mechanical attachments including one or more conductors for delivery of high frequency energy from the source of high frequency to the instrument;

a cable extending from the first part of the qualifying connection for connecting the qualifying connection and the instrument, the cable including electrical conductors for carrying high frequency energy passing through the first part of the qualifying connection from the source of high frequency energy to the cable and the instrument;

an identifying circuit in the source of high frequency energy, the identifying circuit coupled to the second part, the identifying circuit responsive to invisible light optically communicated across the optical couplings for verifying the type of instrument connected by the cable, through the qualifying connection to the source of high frequency energy, the identifying circuit for signaling the verification to the source of high frequency energy;

a memory coupled within the identifying circuit, the memory for receiving and comparing verification signals to predetermined instrument identification therewithin, and a switch in the source of high frequency energy and connected to the memory, the switch connected within the source of high frequency energy for controlling activation and deactivation of the flow of high frequency energy therefrom through at least one of the mechanical attachments, the cable and to the instrument, the switch responsive to the signals of the identifying circuit thereby activating or deactivating the source of high frequency energy.

12. A system including a source of high frequency energy and a qualifying connection for an instrument attached to the source of high frequency energy for electrosurgery and surgical signals from the source of high frequency energy delivered through the qualifying connection to and from the instrument, the connection having a first part connectable to the instrument and a second part on the source of high frequency energy, the qualifying connection comprising:

mechanical attachments on the first and second parts for geometrically conjugating, the mechanical attachments extending across the qualifying connection for juxtapositioning the first and second parts of thereof, the mechanical attachments on the second part connected to the source of high frequency energy, the mechanical attachments on the first part coupled to the instrument for delivery of high frequency energy;

optical couplings on the first and second parts for passing invisible optical energy thereacross to communicate instrument identity, the optical couplings geographically oriented proximate relative to the juxtaposed first and second parts for communicating when the mechanical attachments conjugate;

an infrared light supply in the source of high frequency energy, the infrared light supply connected to the optical couplings in the second part for transmission across the communicating optical couplings;

an infrared light modifier on the optical couplings on the first part, the infrared light modifier positioned proximal for coding of the transmitted infrared light communicated across the optical couplings;

a cable extending from the first part for connecting the qualifying connection and the instrument, the cable for carrying high frequency energy from the mechanical attachments to the instrument, the cable for allowing movement of the instrument relative to the source of high frequency energy;

an identifying circuit in the source of high frequency energy second part and connected to respond to infrared light optically coded by the infrared light modifier, the identifying circuit for verifying the type of instrument connected by the cable through the qualifying connection to the source of high frequency electrosurgical energy, the identifying circuit connected for signaling the verification to the source of high frequency energy, and a switch in the source of high frequency energy coupled to the identifying circuit for responding to the signals of the identifying circuit, the switch connected within the source of high frequency energy for enabling and disabling the flow of high frequency energy from the source of high frequency energy through at least one of the mechanical attachments, the cable and to the instrument.

13. A system including a source of medical treatment and a qualifying connection between an instrument and the source of medical treatment, the qualifying connection for passage of treatment from the source of medical treatment through the qualifying connection to the instrument, the qualifying connection for selectively permitting passage of information from the instrument to the source of medical treatment, the qualifying connection comprising:

a first part of the qualifying connection connectable to the instrument;

a second part of the qualifying connection carried on and connected to the source of medical treatment;

a transmitter on the source of medical treatment second part for delivery of informational energy to the first part on the instrument;

a modifier on the first part proximately positioned relative to the transmitter, the modifier able to change the energy from the transmitter;

one or more receivers on the second part located for receipt of the changed energy from the modifier;

mechanical attachments across the qualifying connection for juxtapositioning the first and second parts thereof, the mechanical attachments having geometric conjugations for delivering medical treatment through the qualifying connection from the source of medical treatment to the instrument, the mechanical attachments for positioning proximally and geographically the first part on the instrument and the second part on the source of medical treatment when the mechanical attachments conjugate so that the first and second parts may communicate across the qualifying connection between the first and second parts for transmitting and receiving information and changed energy thereacross thus communicating the identity of the instrument to and medical treatment from the source of medical treatment;

an identifying circuit connected to the second part thus located in the source of medical treatment for receiving communicated information from the receiver, the identifying circuit responsive to communicated information for differentiating the type of instrument connected by the mechanical attachments through the qualifying connection to the source of medical treatment, the identifying circuit for generating a signal of verification to the source of medical treatment, and a switch in the source of medical treatment responsive to the signaling of the identifying circuit, the switch connected to the identifying circuit within the source of medical treatment, the switch connected within the source of medical treatment for controlling the passage of medical treatment from the source of medical treatment through at least one of the mechanical attachments and to the instrument.

14. The qualifying connection of claim 13 wherein the switch in the source of medical treatment is connected to an energy provider in the source of medical treatment responsive to the automatic activation of the source of high frequency energy by the identifier circuit for setting the nature of the energy conveyed in accord with the instrument identified and for differentiating the instrument attached through the qualifying connection from other unqualified instruments.

15. The qualifying connection of claim 14 wherein the transmitter delivers light in the infrared wavelengths and the modifier is a surface on the first part positioned proximal the transmitter on the second part, the surface configured to modify the delivered light by absorption, diffraction, reflection or a combination thereof.

16. The qualifying connection of claim 15 wherein the mechanical attachments include one or more electrical conductors and the energy provider includes an electrosurgical generator for delivery of modes of radio frequency electrosurgery across the mechanical attachments.

17. The qualifying connection of claim 15 wherein the mechanical attachments include one or more wave guides and the energy provider is a laser for delivery of light energy through the mechanical attachments.

18. The qualifying connection of claim 15 wherein the mechanical attachments include one or more fluid passages and the energy provider is a fluid movement apparatus for delivery of suction or irrigation through the mechanical attachments.

19. The qualifying connection of claim 15 wherein the mechanical attachments include one or more energy couplings and the energy provider is a microwave generator for delivery of microwaves through the mechanical attachments.

20. The qualifying connection of claim 15 wherein the mechanical attachment include male and female portions.

21. The qualifying connection of claim 15 wherein the modifier is located in the first part sandwiched between the transmitter and receiver on the second part.

22. The qualifying connection of claim 15 wherein the surface includes a matrix for modifying the light in the infrared wavelengths.

23. The qualifying connection of claim 13 wherein the receivers include fiber optics extending between the second part and the source of medical treatment, and detectors located in the source of medical treatment are connected to the fiber optics so that the space required for the detectors is uninhibited by the second part.

24. The qualifying connection of claim 13 wherein the receivers include fiber optics extending between the second part and the source of medical treatment, the fiber optics have several groups of multiple redundant fibers for simultaneously passage of the information from the modifier in the form of modified light, a plurality of cells within the source of medical treatment so each group of the multiple redundant fibers may extend to a particular cell and deliver thereto modified light as coded identity information.

25. A non-contact recognition system for identifying a connection between a surgical instrument and a generator for applying energy to the surgical instrument, the system comprising:

a first connection part connected to the surgical instrument;

a second connection part connected to the generator;

the first connection part including a first optical coupling, the first optical coupling including a light modifier in the form of a diffuse surface, the diffuse surface including a light responsive medium having an identification code indicative of the surgical instrument, the first connection part insertable into the second connection part;

the second connection part including a light supply and a light receptor, the light supply transmitting a non-focused light beam to the diff-use surface of the first connection part and the diffuse surface modifying the light received from the second part, the light receptor receiving the non-focused light beam modified by the diffuse surface; and an identifying circuit in the generator responsive to the modified light communicating through the first and second connection parts to identify the surgical instrument connected to the generator.

26. The system according to claim 25, wherein the light responsive medium includes a coating for modifying the light energy.

27. The system according to claim 25, wherein the light responsive medium includes a matrix of holes for modifying the light energy.

28. The system according to claim 25, wherein the light supply includes a plurality of infrared transmitters and the light modifier changes the energy transmitted from the transmitters.

29. The system according to claim 25, wherein the light includes a plurality of non-contact detectors.

30. The system according to claim 29, further comprising a memory in the generator for receiving and processing the modified light reflected by the diffuse surface controlling the activation and deactivation of the generator.

31. The system according to claim 30, wherein the memory compares the coded signals of the diffuse surface to a predetermined instrument identification therein.

32. The system according to claim 25, wherein the generator provides high frequency energy to the surgical instrument.

33. The system according to claim 25, wherein the first connection part further includes a male mechanical attachment for reception in a female portion on the second connection part to position the first optical coupling of the first connection part and a second optical coupling of the second connection part in proximity.

34. The system according to claim 33, further comprising a switch electrically connected to the identifying circuit in the generator, the switch enabling the passage of energy from the generator through the mechanical attachment and to the surgical instrument.

35. The system according to claim 25, wherein the optical energy is invisible infrared optical energy.

36. The system according to claim 35, wherein the identifying circuit responds to infrared light optically coded by the infrared light modifier.

37. The system according to claim 36, wherein the second connection part includes a plurality of transmitters and the light modifier changes the light energy from the transmitters.

38. The system according to claim 34, wherein the switch allows setting the nature of the energy conveyed to the surgical instrument.

39. The system according to claim 25, further comprising a plurality of receivers on the second connection part and the light supply includes a plurality of transmitters, the light modifier being located proximate the transmitters and receiver.

40. The system according to claim 39, wherein the receivers include a plurality of optical fibers.

41. A system according to claim 25, further comprising a display to provide a visual indication that the correct instrument is attached to the generator.

42. The system according to claim 25, wherein the identification code of the first connection part has Nth bit code identification unique to the type of surgical instrument.

43. The system according to claim 42, wherein upon receiving the surgical instrument identity the information is hardware and software processed to determine if the identity code is correct and whether the electrosurgical energy should be supplied.

44. The system according to claim 43, wherein the first connection portion is in the form of a plug and Nth bit code identity is located on the plug.

45. A method of identifying a surgical instrument for determination of application of energy comprising:

providing a first connection part having a light modifier in the form of a diffuse surface corresponding to a predetermined code particular to the type of instrument;

providing a generator having a second connection part having a plurality of transmitters for transmitting an unfocused beam of light to the diff-use surface;

inserting the first connection part into the second connection part so the diffuse surface and the transmitters are in proximity;

transmitting optical energy from the transmitters of the second part to the diff-use surface of the first part;

processing the modified light in the generator to determine the type of surgical instrument connected to the generator; and controlling the activation and deactivation of the generator in response to the determination of the type of surgical instrument.

46. A system according to claim 45, further comprising the step of providing a visual indication that the correct instrument is attached to the generator.

47. A system according to claim 45, wherein the step of transmitting optical energy includes transmitting optical energy to a coating on the diffuse surface.

48. A system according to claim 45, wherein the step of transmitting optical energy includes transmitting optical energy to a matrix of holes.

* * * * *